United States Patent
Helmer et al.

(10) Patent No.: US 12,230,063 B2
(45) Date of Patent: Feb. 18, 2025

(54) EYE-TRACKING DEVICE AND METHOD

(71) Applicant: Sanofi, Paris (FR)

(72) Inventors: Michael Helmer, Frankfurt am Main (DE); Martin Vitt, Frankfurt am Main (DE)

(73) Assignee: Sanofi, Paris (FR)

(*) Notice: Subject to any disclaimer, the term of this patent is extended or adjusted under 35 U.S.C. 154(b) by 80 days.

(21) Appl. No.: 17/786,047

(22) PCT Filed: Dec. 17, 2020

(86) PCT No.: PCT/EP2020/086825
§ 371 (c)(1),
(2) Date: Jun. 16, 2022

(87) PCT Pub. No.: WO2021/123022
PCT Pub. Date: Jun. 24, 2021

(65) Prior Publication Data
US 2023/0017183 A1 Jan. 19, 2023

(30) Foreign Application Priority Data
Dec. 19, 2019 (EP) .................... 19306688

(51) Int. Cl.
*G06F 3/01* (2006.01)
*G06T 7/246* (2017.01)
*G06V 40/19* (2022.01)

(52) U.S. Cl.
CPC .............. *G06V 40/19* (2022.01); *G06F 3/013* (2013.01); *G06T 7/246* (2017.01)

(58) Field of Classification Search
CPC .......... G06F 3/013; G06F 3/012; G06F 3/005; G06F 3/0481
See application file for complete search history.

(56) References Cited

U.S. PATENT DOCUMENTS

| 10,039,445 B1* | 8/2018 | Torch ....................... G06F 3/017 |
| 2015/0293589 A1* | 10/2015 | Zhou ..................... G06F 3/0304 |
| | | 345/157 |

(Continued)

FOREIGN PATENT DOCUMENTS

| CN | 109445583 | 3/2019 |
| EP | 2849030 | 3/2015 |

(Continued)

OTHER PUBLICATIONS

International Preliminary Report on Patentability in International Appln. No. PCT/EP2020/086825, mailed on Jun. 30, 2022, 8 pages.

(Continued)

*Primary Examiner* — Kevin M Nguyen
(74) *Attorney, Agent, or Firm* — Fish & Richardson P.C.

(57) ABSTRACT

A device comprising at least one camera, a display, a memory and a processor, the memory storing instructions which, when executed by the processor, cause the device to: display, using the display of the device, a content to be reviewed by the user; detect, using the camera of the device, user's eyes; detect, using the camera of the device, user's eye movements; determine, based on the detected user's eye movements, whether the user has reviewed the content.

20 Claims, 2 Drawing Sheets

(56) References Cited

U.S. PATENT DOCUMENTS

| | | | |
|---|---|---|---|
| 2015/0331240 A1 | 11/2015 | Poulos et al. | |
| 2016/0246384 A1 | 8/2016 | Mullins et al. | |
| 2018/0328751 A1* | 11/2018 | Bejot | ............... G06T 13/40 |

FOREIGN PATENT DOCUMENTS

| | | |
|---|---|---|
| JP | 2012-198608 A | 10/2012 |
| JP | 2013-025656 A | 2/2013 |
| JP | 2018-524712 A | 8/2018 |
| WO | WO 2018/046957 | 3/2018 |

OTHER PUBLICATIONS

International Search Report and Written Opinion in International Appln. No. PCT/EP2020/086825, mailed on Mar. 25, 2021, 10 pages.

* cited by examiner

EYE-TRACKING DEVICE AND METHOD

CROSS REFERENCE TO RELATED APPLICATIONS

The present application is the national stage entry of International Patent Application No. PCT/EP2020/086825, filed on Dec. 17, 2020, and claims priority to Application No. EP 19306688.3, filed on Dec. 19, 2019, the disclosures of which are incorporated herein by reference.

TECHNICAL FIELD

The present disclosure is generally related to eye-tracking devices and methods. In particular, the disclosure relates to devices and methods that be used e.g., for supervised training.

BACKGROUND

Users of various drug delivery devices, such as insulin pens and the like, require users to be trained in use of the device. Such training may be necessary and/or beneficial especially when the user is first issued with a particular device (e.g., a newly diagnosed patient, or a user who has been using a drug delivery device for some time but has been recommended to switch to a different, unfamiliar device, different drug and/or different dosage regime).

SUMMARY

For various reasons, it may be beneficial or required to supervise the training and/or make sure the user completes all required sections of the training. For example, it may be required by a regulatory body that the user, the manufacturer or both are issued a certificate of the user having completed a standardized training.

Currently, the drug delivery device training is usually provided by a health care professional (such as a nurse). Such training may be time consuming and inefficient for the health care professional. Further, it may be difficult for the health care professional to verify whether the user has understood all the training content required.

There is therefore a need to provide an automated, standardized training.

In a first aspect, a device is provided, the device comprising at least one camera, a display, a memory and a processor, the memory storing instructions which, when executed by the processor, cause the device to: display, using the display of the device, a content to be reviewed by the user; detect, using the camera of the device, user's eyes; detect, using the camera of the device, user's eye movements; determine, based on the detected user's eye movements, whether the user has reviewed the content.

In a second aspect, a device is provided, the device comprising at least one camera, a motion sensor, a display, a memory and a processor, the memory storing instructions which, when executed by the processor, cause the device to: display, using the display of the device, a content to be reviewed by the user; detect, using the camera of the device, the motion sensor of the device, or both the camera and the motion sensor, user's eyes; detect, using the camera of the device, the motion sensor of the device, or both the camera and the motion sensor, user's eye movements; determine, based on the detected user's eye movements, whether the user has reviewed the content.

In some embodiments, the first aspect and the second aspect may be combined with one or more of the following features:

the at least one camera comprises at least one front camera;
detecting the user's eye movements comprises detecting one or more of the following: the direction of the user's gaze, the speed of the user's eye movements, the direction of the user's eyes movements, the time spent by the user focusing on a content, the timing of the user's blinking, the rate of the user's blinking, duration of pupil fixation, number of pupil fixations, view path, pupil diameter and stress load, and/or dwell time;
determining whether the user has reviewed the content comprises monitoring duration of a blink of the user's eyes;
determining whether the user has reviewed the content further comprises comparing the value to a pre-stored average value of eye blink duration;
if the duration of the user's eye blink is above 0.5 seconds, the user is determined not to have reviewed the content;
determining whether the user has reviewed the content further comprises comparing the value to a pre-stored average value of eye blink duration, and if the duration of the user's eye blink is above 0.5 seconds, the user is determined not to have reviewed the content;
determining whether the user has reviewed the content comprises monitoring a blink rate of the user's eyes;
determining whether the user has reviewed the content further comprises comparing the value to a pre-stored average value of a blink rate;
determining whether the user has reviewed the content comprises monitoring a blink rate of the user's eyes, and determining whether the user has reviewed the content further comprises comparing the value to a pre-stored average value of a blink rate;
determining whether the user has reviewed the content comprises monitoring the pupil diameter of the user's eyes;
determining whether the user has reviewed the content further comprises comparing the value to a pre-stored value of a pupil diameter;
determining whether the user has reviewed the content comprises monitoring the pupil diameter of the user's eyes, and determining whether the user has reviewed the content further comprises comparing the value to a pre-stored value of a pupil diameter;
determining whether the user has reviewed the content comprises monitoring the number of eye fixations;
the content comprises a text and determining whether the user has reviewed the content further comprises comparing the number of eye fixations to the number of words in the text;
if the number of eye fixations corresponds to 80% to 100% of the number of words in a text, the user is determined to have reviewed the content;
determining whether the user has reviewed the content comprises monitoring the number of eye fixations, and when the content comprises a text, determining whether the user has reviewed the content further comprises comparing the number of eye fixations to the number of words in the text;
determining whether the user has reviewed the content comprises monitoring the number of eye fixations, when the content comprises a text, determining whether the user has reviewed the content further comprises comparing the number of eye fixations to the number of words in the text, and if the number of eye fixations corresponds to 80% to 100% of the number of words in a text, the user is determined to have reviewed the content;

determining whether the user has reviewed the content comprises monitoring the duration of eye fixations;

if the duration of the user's eye fixation is between 200 milliseconds and 250 milliseconds for at least 80% of fixations, the user is determined to have reviewed the content; and the device further comprises a motion sensor and wherein the device is adapted to detect the user's eye movements using the camera of the device and the motion sensor.

In a third aspect, a method of determining whether a user has reviewed a content is provided, the method comprising: displaying a content to be reviewed by the user; detecting user's eyes; detecting user's eye movements; determining, based on the detected user's eye movements, whether the user has reviewed the content.

The method of the third aspect may use one or more of the following specific features:

determining whether the user has reviewed the content comprises monitoring a blink rate of the user's eyes;

determining whether the user has reviewed the content comprises monitoring the pupil diameter of the user's eyes;

determining whether the user has reviewed the content comprises monitoring the number of eye fixations; and determining whether the user has reviewed the content comprises monitoring the duration of eye fixations.

BRIEF DESCRIPTION OF THE FIGURES

The following description is with reference to the following Figures.

DETAILED DESCRIPTION

Figure 1:
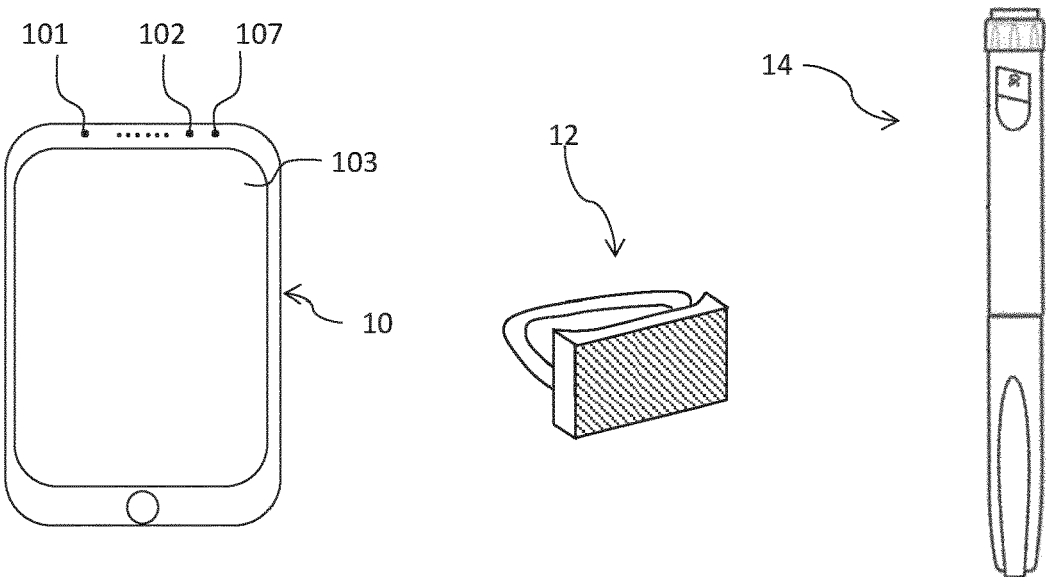
FIG. 1 shows an example system of a mobile device, augmented reality, virtual reality or mixed reality glasses and a training drug delivery device.

FIG. 1 shows a training system comprising an augmented reality (AR), virtual reality (VR) or mixed reality (MR) glasses 12, a user device 10 and a training drug delivery device 14. AR, VR or MR glasses 12 will hereinafter be referred to as glasses 12. If the system comprises the glasses 12, the user device 10 may be optional. If the system comprises the user device 10, the glasses 12 may be optional. The training drug delivery device 14 is optional.

The glasses 12 may be a head mount for a mobile device, such as a user device 10. The system may comprise both the glasses 12 and the user device 10. The glasses 12 may be a device independent of a mobile device. If the glasses 12 are independent of a mobile device, the user device 10 may be optional.

The user device 10 may be for example a mobile device, such as mobile phone or tablet. The user device 10 may be a desktop PC.

For the sake of conciseness, the following is described with reference to the user device 10 only. It is to be understood that in the following, the user device 10 could be replaced with the glasses 12, or with a system comprising the user device 10 and the glasses 12.

The user device 10 has a camera 101 associated with the user device 10. The camera 101 may be a front camera of a mobile device, i.e. the camera may be provided as a part of the same side of the user device 10 as its display 103. The camera 101 may be capable of aiming at the user when the user device 10 is in use. The camera 101 may be a webcam or any other suitable external camera associated with a mobile device or a desktop PC.

In an embodiment, the user device 10 has a light source 102 associated with the user device 10. The light source 102 may be provided as part of the user device 10. The light source 102 may be provided as a separate device; in that case, the light source 102 is preferably adapted to be attached to the user device 10 and/or the glasses 12. The light source 102 may be provided as part of the glasses 12. The light source 102 may be an infra-red (IR) light source. The light source 102 may be a laser light source.

The user device 10 has a display 103. In an embodiment, the IR light may be additionally or exclusively provided by the display 103 of the user device 10. For example, if the display 103 is a LED or OLED display, it may be possible to use the display 103 as a source of the IR light. The IR light may come partially or exclusively from the display 103.

The user device 10 may have a motion sensor 107. The motion sensor may be e.g., a radar sensor 107.

Figure 3:
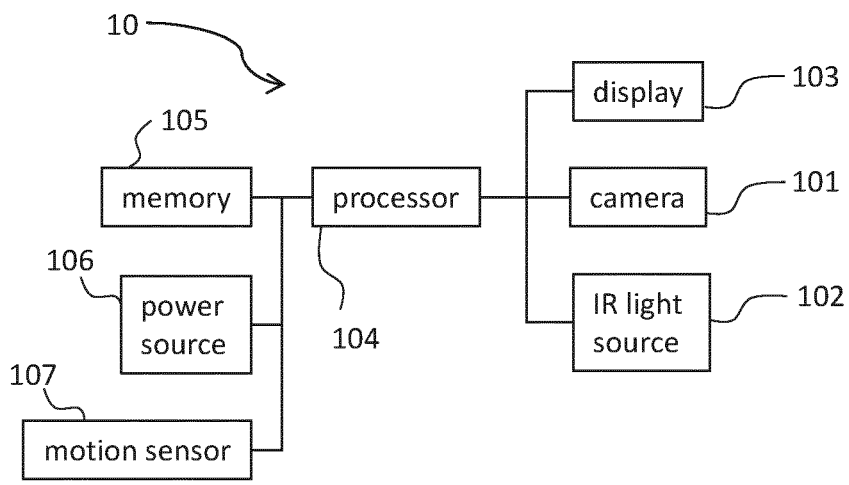
FIG. 3 is a schematic representation of electronic components of a user device.

The user device 10 further comprises a processor 104, a memory 105 and a power source 106. These components are shown in FIG. 3 and further described below.

The user device 10 has a memory 105 which stores one or more suitable software applications to execute methods described below.

Using the camera 101, the motion sensor 107 or both the camera 101 and the motion sensor 107, the user device 10 may monitor the eyes of the user. The user device 10 may monitor the position of the user's eyes. The user device 10 may monitor the user's eye movements. The user device 10 may use the camera 101 to monitor the position of the user's eyes and the user's eye movements. The user device 10 may use the camera 10 to monitor the position of the user's eyes, and the motion sensor 107 to monitor the user's eye movements (e.g., movement of the user's eyes and/or the user's eyelids, as described below).

In an embodiment, the user device 10 comprises at least two front cameras 101. The user device 10 may use the at least two cameras 101 to monitor the position and/or movements of the user's eyes. Alternatively or in addition, the user device may use the motion sensor 107 to monitor the user's eye movements (e.g., movement of the user's eyes and/or the user's eyelids). Using two cameras may enable providing a stereoscopic image, which may improve the precision and efficiency of measuring of the user's eye movements. Using the motion sensor 107 may further improve precision in detection of the user's eye movements (e.g., movement of the user's eyes and/or the user's eyelids).

Hereinafter, the user's eye movements mean one or more of the following: the direction of the user's gaze, the speed of the user's eye movements, the direction of the user's eyes movements, the time spent by the user focusing on (reading or watching) a content, the timing of the user's blinking, the rate of the user's blinking, duration of pupil fixation, number of pupil fixations, view path, pupil diameter and stress load; and dwell time (per content).

Hereinafter, monitoring user's eye movements means monitoring one or more of the user's eye movements listed above.

The obtained data regarding the user's eye movements may be used in determining whether the user has spent sufficient time on specific training content. The obtained data regarding the user's eye movements may be used in determining whether the user's attention to the training content has been sufficient. Using the obtained user's eye movements measurements, the user device 10 may be able to determine whether the user has read or watched all training contents of the training. Using the obtained user's eye movement measurements, the user device 10 may be able to determine whether the user has understood all training contents. Using the detected user's eye movement measurements, the user device 10 may be able to determine the likelihood that the user has understood the training contents.

Figure 2A:
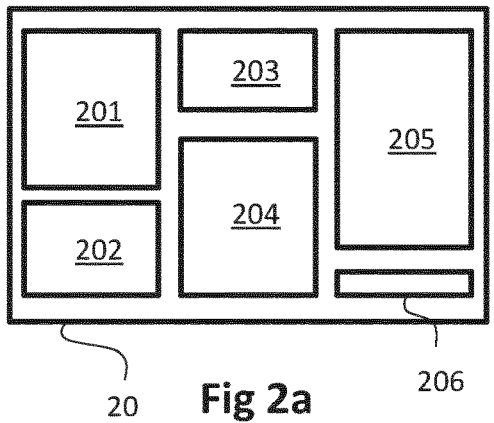
FIG. 2 shows a schematic example of supervised reading.
Figure 2B:
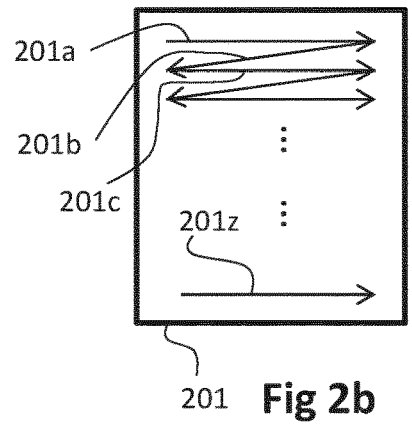

An example of monitoring the user's eye movements using the camera 101 and/or the motion sensor 107 and the user device 10 is shown in FIGS. 2a to 2d. FIG. 2a shows a training content 20 which may be displayed on a display 103 of the user device 10. The training content 20 consists of blocks of text 201-206. To successfully complete the training, the user is required to read and understand all the blocks of text 201-206. For example, the training content 20 may relate to use of an insulin pen, and may comprise drug-related information, device-related information, contraindication information etc.

When the user starts reading block 201, the camera 101 and/or the motion sensor 107 tracks the user's eye movements. The user's eyes move generally along the lines of the text in block 201, as indicated by arrows 201a-201z in FIG. 2b. The user's device 10 tracks the user's eye movements along these lines 201a-201z.

To determine whether the user has read and understood block 201, the user device 10 may store information about average time necessary to read and understand the text in block 201. For example, if the user spends the average time necessary to read and understand the text in block 201 or more than the average time necessary to read and understand the text in block 201, the user device 10 may indicate that the user has successfully completed block 201.

The user device 10 may use alternative or additional information, such as the user's eye movements (described above) to determine whether the user had read and understood the text in block 201. If the user spends less than the average time necessary to read and understand the text in block 201, the user device 10 may use further information such as user's eye movements to determine whether the user has read and understood all the training content in block 201.

The user device 10 may use alternative or additional information, such as the user's eye movements (described above) to determine whether the user had read and understood the text in block 201 regardless of the time it takes the user to read the block 201.

For example, if the user needs the average time necessary to read and understand the text in block 201 and the pupil diameter indicates that the user has paid attention to the text, the user device 10 may indicate that the block 201 has been successfully completed.

As another example, if the user needs more than average time necessary to read and understand the text in block 201, but the pupil diameter indicates that the user has not paid attention to the text, the user device 10 may indicate that the block 201 has not been successfully completed.

As another example, if the user needs less than the average time necessary to read and understand the text in block 201, but the pupil diameter indicates that the user has not paid attention to the text, the user device 10 may indicate that the block 201 has not been successfully completed.

Figure 2C:
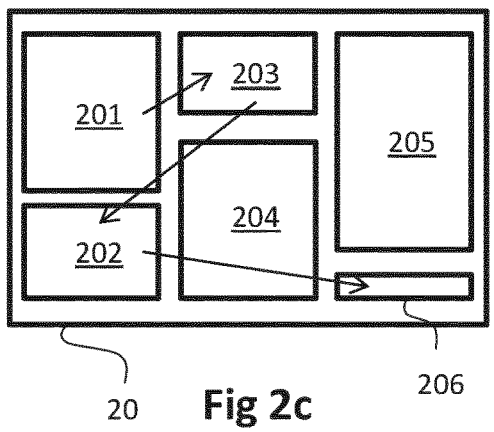

In the example of FIG. 2, after reading block 201, the user's eyes continue to block 203, as illustrated in FIG. 2c. The user reads block 203. The successful or unsuccessful completion of block 203 is assessed and indicated in a manner similar to block 201, as described above.

As further illustrated in FIG. 2c, after reading block 203, the user continues to block 202, and reads the text in block 202. After reading block 202, the user continues to block 206, and reads block 206. The successful or unsuccessful completion of block 202 and 206 is assessed and indicated in a manner similar to block 201, as described above.

In the example of FIG. 2c, the user does not read blocks 204 and 205, which is assessed and indicated in a manner similar to block 201, as described above.

Figure 2D:
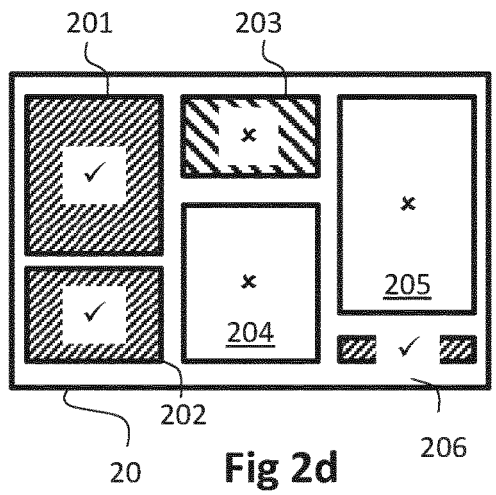

FIG. 2d shows one possible indication of the outcome of assessment of the user's reading and understanding of the information. Based on the measurement of the user's eye movements (described above), the user device 10 determines that the user has read and understood blocks 201, 202 and 206; the user has read but not understood block 203; and that the user has not read blocks 204 and 205. The user device 10 may then indicate the status of each block 201-206, and display the information on the display 103 of the user device 10.

The status of each block 201-206 may be indicated in different colours (e.g., green for blocks 201, 203, 206 which the user has read and understood; red for blocks 204, 205 which the user has not read; and red or orange for block 203 which the user has read but not understood). Alternatively or in addition, the status of each block 201-206 may be indicated by different textures, different background pictures, tick/cross marks displayed over the blocks 201-206, or in any other suitable way.

Preferably, the training is indicated as accomplished when the user has read and understood all blocks 201-206. In case the user does not read and understand all the blocks 201-206, the user may be allowed and/or prompted to return to the training at a later time.

Alternatively or in addition, the user device 10 may use the user's eye movements monitoring with other content than written content. For example, the user may be required to review a training video where correct use of a drug delivery device is demonstrated and/or in which an avatar (e.g., simulating a health care professional) explains drug-related or drug delivery device-related information to the user. The user's attention can be focused on the drug delivery device and/or the avatar shown in the video, as appropriate. The user's eye movements may be monitored in a manner similar to that described above to assess whether the user's attention is focused on the right object or objects (e.g., the drug delivery device shown, the avatar shown, etc.). For example, if the user is determined to look elsewhere than at the drug delivery device or the avatar for most of the duration of the training video, the user device 10 may determine that the user has not paid attention and that the viewing of the video needs to be repeated.

Figure 4:
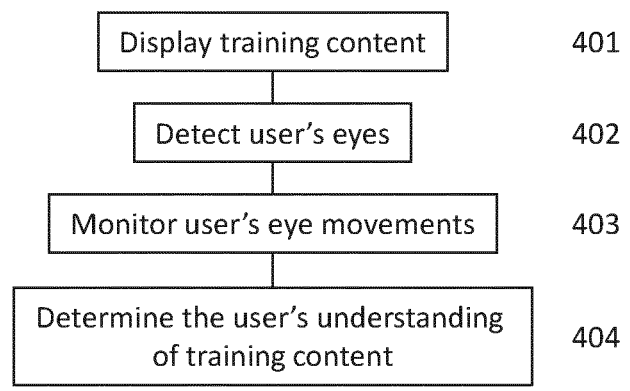
FIG. 4 is a flow chart showing a method of supervising a user's training.

The method of determining the user's understanding of a training content is illustrated in FIG. 4.

The user device 10 has a processor 104 and a memory 105. The memory 105 stores instructions which, when executed by the processor 104, perform the following methods.

In step 401, the user device 10, using the display 103, displays the training content. In step 402, the user device 10, using the camera 101 and/or the motion sensor 107, detects the user's eyes. In step 403, the device, using the camera 101 and/or the motion sensor 107, monitors the user's eye movements, for example as described above in connection with FIGS. 2a to 2d. In step 404, the user's understanding of the training content displayed on the display 103 in step 401 is determined, for example as described above in connection with FIGS. 2a to 2d.

Monitoring the user's eye movements and/or determining whether the user has read and understood content may comprise one or more of the following, in any combination. The description below is provided with focus on a text content, but it will be understood that same or analogous considerations apply to a picture/video content.

The duration of a blink of the user's eyes may be measured. For example, typical duration of the blink (i.e. the time elapsed between the moment the lid closes fully and the moment the lid starts to open again) in an attentive reader may be 0-0.2 seconds. Duration of the blink in a user who is unfocused may be typically 0.3-0.5 seconds. Duration of the blink in a tired person may be >0.5 seconds. By detecting duration of the blink and comparing the values to typical values such as described above (e.g., pre-stored average, or a pre-stored bench mark of a specific user), the user device 10 may be able to determine whether the user has paid attention to the text. In one embodiment, if duration of the blink exceeds 0.5 seconds, the user device 10 interrupts the training.

The blink rate (i.e. the number of blinks per time unit) may be measured. For example, a higher and/or increasing blink rate may be an indication of alertness (the user is paying attention to the text). A lower and/or decreasing blink rate may be an indication that the user is not paying attention and/or the user lacks understanding of the text. In an embodiment, the user device 10 may detect the user's blink rate and compare the measured value to a typical value such as a pre-stored average, a pre-stored bench mark for a specific user, etc. In an embodiment, the user device 10 may interrupt the training if the blink rate is or falls below a threshold.

The pupil diameter of the user's eye may be measured. Typically, an increased pupil diameter may serve as an indication for the user paying attention to the text. For example, if the pupil diameter increases during reviewing of the text, the user device 10 may determine that the user is paying attention to the text.

The number and duration of eye fixations may be measured. For example, a user who is paying attention to the text shows a fixation for at least 80% of words. Therefore, if the number of fixations corresponds to 80% to 100% of the number of words, the user may be determined to have paid attention and/or understood the text. In an embodiment, if the number of fixations is at least 80% of the number of the words, the user is determined to have paid attention and/or understood the text. For example, the duration of a fixation may be 200-250 milliseconds. If the duration of each fixation is consistently shorter than e.g., 200 milliseconds, the user may be determined not to have paid attention and/or not to have understood the text.

In one embodiment, the blink rate, blink duration and pupil diameter may all be measured and used together to determine the level of the user's attention. The level of the user's attention together with the direction of the user's gaze, the speed of the user's eye movements, the direction of the user's eyes movements and the time spent by the user focusing on reading a content may be used to determine whether the user has paid attention to the text and/or understood the text.

In an embodiment, the user device 10 may, after interrupting the training, provide the user with questions related to the text.

In an embodiment, the user's device 10 may cooperate with a training drug delivery device 14. The training drug delivery device 14 is a device which resembles a real drug delivery device which the user will use (e.g., a device which has been prescribed to the user).

The invention claimed is:

1. A device comprising at least two cameras, a display, a memory, and a processor, the memory storing instructions which, when executed by the processor, cause the device to:
   display, using the display of the device, a content to be reviewed by a user, wherein the content comprises training content related to a drug delivery device;
   detect, using the at least two cameras of the device, eyes of the user;
   detect, using the at least two cameras of the device, eye movements of the user, wherein detecting the eye movements of the user comprises:
      generating, using the at least two cameras of the device, stereoscopic images of the eyes of the user; and
      processing the stereoscopic images of the eyes of the user to detect the eye movements of the user; and
   determine, based on the detected eye movements of the user, whether the user has reviewed the content by monitoring blink duration and/or blink rate and comparing with a respective pre-stored average.

2. The device of claim 1, wherein the at least two cameras comprise at least one front camera.

3. The device of claim 1, wherein detecting the eye movements of the user comprises detecting one or more of the following: a gaze direction of a gaze of the user, a speed of the eye movements of the user, a movement direction of the eye movements of the user, a time spent by the user focusing on a content, a timing of blinking of the user, a blinking rate of the user, a duration of pupil fixation, a number of pupil fixations, a view path, a pupil diameter, a pupil stress load, or a dwell time.

4. The device of claim 1, wherein determining whether the user has reviewed the content comprises monitoring a pupil diameter of the eyes of the user.

5. The device of claim 1, wherein determining whether the user has reviewed the content comprises monitoring a number of eye fixations.

6. The device of claim 1, wherein determining whether the user has reviewed the content comprises monitoring a duration of eye fixations.

7. The device of claim 1, wherein the device further comprises a motion sensor and wherein the device is adapted to detect the eye movements of the user using the camera of the device and the motion sensor.

8. The device of claim 1, wherein the drug delivery device comprises an insulin pen.

9. A device comprising at least two cameras, a motion sensor, a display, a memory and a processor, the memory storing instructions which, when executed by the processor, cause the device to:
   display, using the display of the device, a content to be reviewed by a user, wherein the content comprises training content related to a drug delivery device;
   detect, using the at least two cameras of the device, the motion sensor of the device, or both the at least two cameras and the motion sensor, eyes of the user;
   detect, using the at least two cameras of the device, eye movements of the user, wherein detecting the eye movements of the user comprises:

generating, using the at least two cameras of the device, stereoscopic images of the eyes of the user; and processing the stereoscopic images of the eyes of the user to detect the eye movements of the user; and determine, based on the detected eye movements of the user, whether the user has reviewed the content by monitoring blink duration and/or blink rate and comparing with a respective pre-stored average.

10. The device of claim 9, wherein the motion sensor comprises a radar sensor.

11. The device of claim 9, wherein detecting the eye movements of the user comprises detecting one or more of the following: a gaze direction of a gaze of the user, a speed of the eye movements of the user, a movement direction of the eye movements of the user, a time spent by the user focusing on a content, a timing of blinking of the user, a user blinking rate, a duration of pupil fixation, a number of pupil fixations, a view path, a pupil diameter, a pupil stress load, or a dwell time.

12. The device of claim 9, further comprising a light source configured to illuminate the eyes of the user.

13. The device of claim 12, wherein the light source comprises an infra-red light source or a laser light source.

14. The device of claim 12, wherein the light source is integrated in the display.

15. A method of determining whether a user has reviewed a content, the method comprising:

displaying a content to be reviewed by the user, wherein the content comprises training content for a drug delivery device;

detecting, using at least two cameras, eyes of the user;

detecting, using the at least two cameras, eye movements of the user, wherein detecting the eye movements of the user comprises:

generating, using the at least two cameras of the device, stereoscopic images of the eyes of the user; and processing the stereoscopic images of the eyes of the user to detect the eye movements of the user;

determining, based on the detected eye movements of the user, whether the user has reviewed the content by monitoring blink duration and/or blink rate and comparing with a respective pre-stored average.

16. The method of claim 15, wherein determining whether the user has reviewed the content comprises monitoring a pupil diameter of the eyes of the user.

17. The method of claim 15, wherein determining whether the user has reviewed the content comprises monitoring a number of eye fixations.

18. The method of claim 15, wherein determining whether the user has reviewed the content comprises monitoring a duration of eye fixations.

19. The method of claim 15, wherein detecting the eye movements of the user comprises detecting one or more of the following: a gaze direction of a gaze of the user, a speed of the eye movements of the user, a movement direction of the eye movements of the user, a time spent by the user focusing on a content, a timing of blinking of the user, a blinking rate of the user, a duration of pupil fixation, a number of pupil fixations, a view path, a pupil diameter, a pupil stress load, or a dwell time.

20. The method of claim 15, wherein detecting eye movements of the user comprises detecting eye movements of the user using at least one camera and at least one motion sensor.

* * * * *